Feb. 1, 1966 A. R. MacBETH Plant Pat. 2,591
LOQUAT TREE
Filed July 21, 1964 2 Sheets-Sheet 1
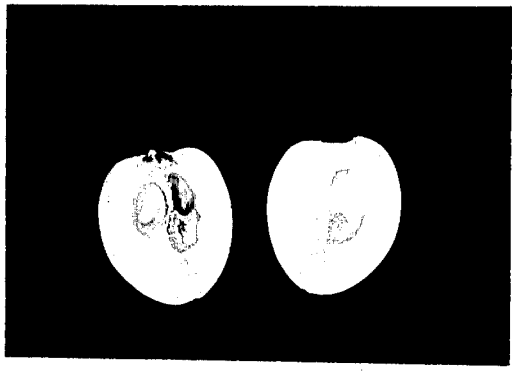
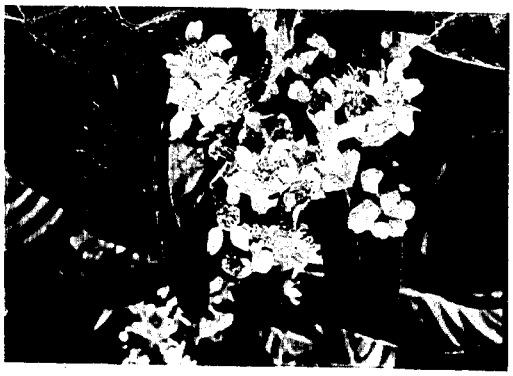
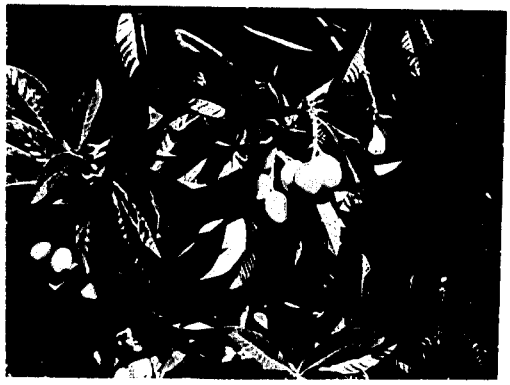
INVENTOR.
ALASTAIR R. MAC BETH
BY J. F. Cuneo
ATTORNEY Feb. 1, 1966 A. R. MacBETH Plant Pat. 2,591
LOQUAT TREE
Filed July 21, 1964 2 Sheets-Sheet 2
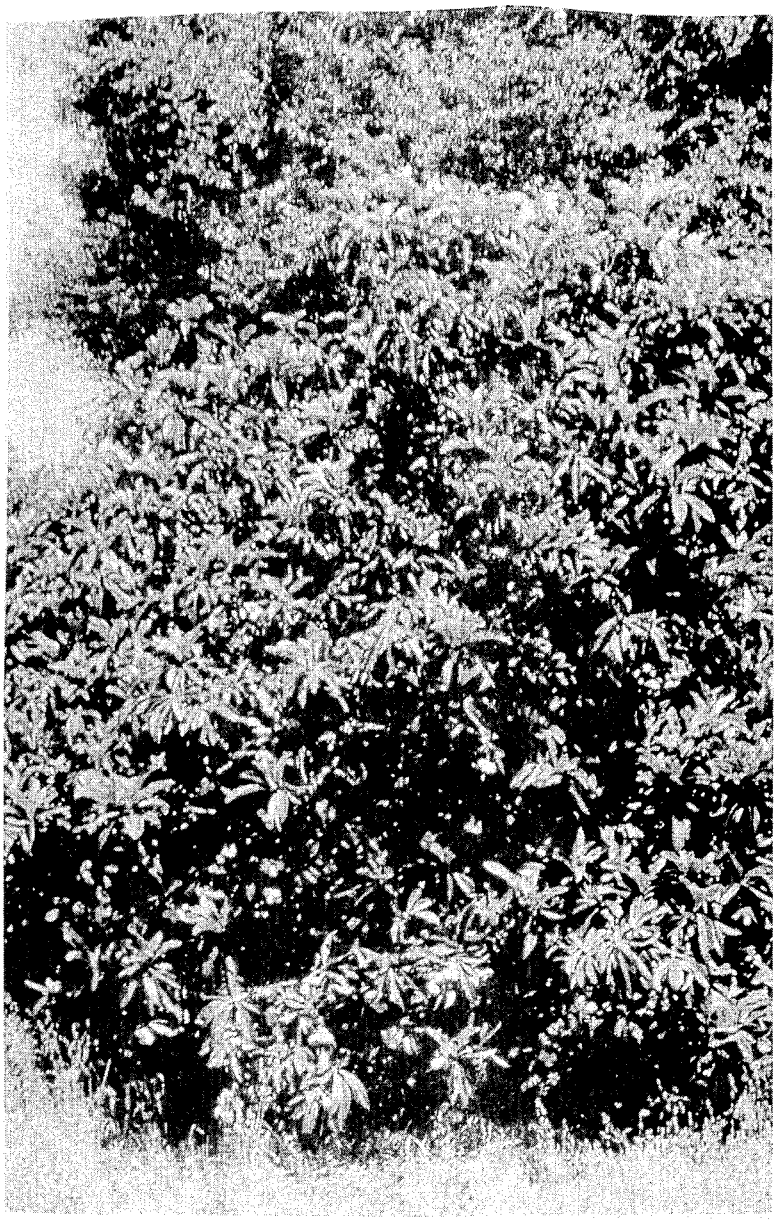
INVENTOR
ALASTAIR R. MAC BETH
BY J. F. Cuneo
ATTORNEY

United States Patent Office

Plant Pat. 2,591
Patented Feb. 1, 1966

2,591

LOQUAT TREE

Alastair R. MacBeth, Carlsbad, Calif., assignor to Select Nurseries, Whittier, Calif., a corporation of California

Filed July 21, 1964, Ser. No. 384,272
1 Claim. (Cl. Plt.—33)

This invention relates to a new and distinct variety of loquat tree.

I discovered the new variety of loquat growing as a chance seedling among a group of cultivated loquat trees on my property located at 1519 Chestnut Street in the city of Carlsbad, county of San Diego, State of California. This discovery was made by me in 1948. The pollen parent of the new variety is unknown, as is the name of the *Eriobotrya japonica* variety which is the presumed seed parent.

The new variety has been asexually produced by me on my property in Carlsbad, California and has also been reproduced asexually in Whittier, California, primarily by grafting on an understock of seedliing of *Eriobotrya japonica*. A large number of grafts have been made since the plant was discovered and in all instances the descendants have exhibited the distinguishing characteristics of the new variety, thus establishing that the strain is true. Thus new variety cannot be reproduced true from seed.

The new and distinct variety is characterized as to novelty particularly by the fact that the fruit is much larger than the fruit of other known species of loquats the flesh of the fruit having a very pleasing flavor which can be best described as mild, and the fruit has a mild acidity. The tree forms a rounded dome-shaped crown, is spreading and presents a bushy appearance. The leaves are large and can be best described as elliptic in form, having an acute apex with a substantially attenuate base. The edges of the leaves are serrate with the teeth spaced quite a distance apart, some teeth being as much as 9/16" apart. One particular characteristic observed in the new variety that has not been observed in any other variety of loquat is that in each leaf, starting usually from the fifth vein from the tip of the leaf on the left hand side, when viewed from the upper side, said vein, instead of continuing as a single straight vein to the margin of the leaf, splits to form a Y at a substantial distance from the margin with the diverging sides of the Y continuing to the margin. The same peculiarity appears less prominently on other veins below the fifth vein on the left hand side but has never been observed on any of the veins on the right hand side.

The accompanying illustrations, three in full color, show a fruit in cross section with some of its seeds exposed; a view of a typical flower cluster and leaves; and a view of a branch with leaves and mature fruit attached. The black and white photograph shows the general appearance of the tree, showing its bushy and spreading habits.

To facilitate identification of the important colors described, the terminology adopted by the British Horticultural Colour Charts has been adopted.

A detailed description of the new and distinct variety of loquat tree follows:

*The tree*

Parentage: Chance seedling discovered among a group of loquat trees.

Habit: The tree has a rounded dome shaped crown and is generally spreading and bushy.

Height: The original tree was first discovered in 1948 and since that time it has reached a height of approximately fifteen feet. The crown is dome-shaped and the tree has a maximum overall diameter of about twenty feet. The general shape of the tree is shown in the black and white illustration.

Trunk: The diameter of the trunk of the new variety varies between six and eight inches and the trunk is covered with a smooth, dark grey bark.

Branches: The main branches of the new variety of loquat are husky and a multitude of smaller branches are present. The first branches on the trunk are approximately four feet from the ground and the skirt formed by these lower branches usually touches the ground.

Foliage:

*Texture.*—The leaves are of average thickness, considering their large size, and are normally glossy.

*Shape.*—The leaves are substantially elliptic, having an acute apex with the base attenuate. The margins of the leaves are serrate with the teeth generally widely spaced; sometimes the teeth are as much as 9/16" apart.

*Arrangement.*—The leaves are opposite.

*Size.*—Fully grown leaves vary from six to ten inches in length and vary from two to four inches in width at the widest portion of the leaf.

*Color.*—The leaves are a brownish green color; the closest shade in the charts is Sage Green ooo861 on the upper side. The underside of the leaves is slightly lighter than the top and is approximately Sage Green ooo861/1.

*Petioles.*—The petioles are somewhat short, usually averaging 1/4" in length.

*Veins.*—The veins on the underside of the leaf are very prominent. The veins on the upper side of the leaf are slightly less prominent. The venation of the leaf is described as pinnate. A particular characteristic of this new variety of loquat is the unusual venation of the leaves; when these are viewed from the upper side, the fifth vein from the tip of the leaf on the left hand side does not continue to the margin as a single vein but instead branches to form a Y at a point a substantial distance from the margin with the two diverging legs of the Y proceeding to the margin, whereas the veins on the right hand side of the leaf usually continue as a single vein to the margin. This branching characteristic is also observed to a somewhat lesser degree on other veins on the left hand side that lie below the fifth vein.

*Vesture.*—The young leaves are highly tomentose on both the upper and lower surfaces and have a soft, wooly hairyness that is more pronounced on the upper side. This hairy condition appears to diminish as the leaf matures and fully developed leaves show practically no hairy covering.

*Rachis.*—The leaves have rachides.

*The flower*

The new variety of loquat blooms profusely in the fall of the year commencing in the latter part of October or the first portion of November.

Blooms:

*Borne.*—In clusters.

*Size of flower.*—Each flower is approximately 3/4" in diameter and has a depth of about 3/8".

*Shape.*—When blooms first open the flowers are cup-shaped; the form of the flowers does not change substantially as the flowers mature.

*Petalage.*—Each flower has five petals. The margins of the petals are entire. Color.—The petals are white and there is little or no discoloration after the flowers are fully matured.

*Form.*—The flowers are single.

*Duration.*—The flowers remain on the stems about two weeks.

*Petaloids.*—None.

*Peduncle.*—The peduncle is sturdy and is approximately 5/16" in length.

*Texture.*—The flowers have a leathery texture.

*Appearance.*—The flowers have a velvety appearance. The blooms are not appreciably affected by hot or wet weather.

*Persistance.*—The flowers hang on to the stem and dry out eventually.

*Fragrance.*—The fragrance of the flowers is very slight.

Bud:

*Form.*—The buds are round and are best described as globular.

*Size.*—The buds are about 1/4" in diameter and have a depth of about 3/8".

*Opening.*—The buds open slowly.

*Color.*—When the sepals first divide, the buds are pale yellow. At the time the petals begin to unfurl, the color is pale yellow.

*Sepals.*—The sepals are hooded over the bud. Color: inside—pale yellow; outside—pale yellow.

*Calyx.*—Shape—the calyx is funnel shaped; it does not split. Aspect—the calyx is hairy.

*Peduncle.*—The penduncle of the bud is 1/8" in length. Aspect—the peduncle is hairy and it is erect. Color—the color of the peduncle is light yellow.

*Genital organs*

Stamens, anthers:

*Arrangement.*—Bunched.

*Length.*—3/16" in length.

*Number.*—Usually 20.

Filaments:

*Length.*—Approximately 3/16" long.

*Color.*—Light yellow.

Pollen: Color—light yellow.

Pistils:

*Number.*—Five in number.

*Length.*—About 3/16".

Stigma: Color—pale green.

Ovaries: Shape—the ovaries are small and oval shaped.

*The fruit*

Shape: The fruit is ovate, resembling an apricot or peach in shape.

Size: The fruit is large, being roughly two inches long and about one and one-half inches in diameter.

Texture: The meat of the fruit has a texture that resembles an apricot or peach.

Color of meat: The principal portion of the flesh of the fruit is light colored and is best identified as Peach 512/3. The intermediate color of the flesh which appears in streaks and spots in the fruit is best identified as Chrome Yellow 605/2. The darker portions of the flesh are Buttercup Yellow 5/2.

Borne: The fruits are borne in clusters of from three to eight and are supported by stems that vary from 1/4" to 3/4" in length. The stems are heavy being approximately 1/8" in diameter. The stems come substantially directly out of the skin of the fruit and do not have any appreciable indentation at the point where the stem leaves the fruit.

Skin:

*Texture.*—The skin is smooth and tough, somewhat resembling a sapota.

*Color.*—The skin is best described as predominantly Saffron Yellow 7/2.

Seeds: The fruits carry from two to four seeds which are relatively small in size when compared to other varieties of loquat. Color—the seeds are a medium dark brown in color.

Taste and flavor: The fruit is very juicy, has a low acidity and is very palatable and pleasing to the taste.

Having described my invention, I claim:

The new and distinct variety of loquat tree substantially as shown and described, characterized particularly as to novelty by the large juicy fruit borne in clusters on husky stems and having a fleshy portion resembling an apricot or peach in texture and having a flavor that is very palatable, the acidity of said fruit being low, and by its large serrate leaves that exhibit a unique venation wherein the fifth vein from the tip of the leaf on the left hand side, when viewed from the upper side of the leaf, instead of continuing to the margin as a single vein, divides to form a Y at a substantial distance from the margin, this Y shaped venation characteristic occurring less prominently on other veins on the left hand side of the leaf that are below said fifth vein but not being present on the veins of the right hand side of the leaf.

No references cited.

ABRAHAM G. STONE, *Primary Examiner.*